United States Patent
Ooi et al.

(10) Patent No.: US 7,255,779 B2
(45) Date of Patent: Aug. 14, 2007

(54) INDOLECARBOXYLIC ESTER TRIMER AND ELECTROCHEMICAL CELL USING THE SAME

(75) Inventors: Hideo Ooi, Shizuoka (JP); Naoto Yazawa, Shizuoka (JP); Masaya Mitani, Sendai (JP); Tomoki Nobuta, Sendai (JP); Toshihiko Nishiyama, Sendai (JP); Tetuya Yoshinari, Sendai (JP); Naoki Takahashi, Sendai (JP)

(73) Assignees: Ihara Chemical Industry Co., Ltd. (JP); NEC Tokin Corporation (JP)

( * ) Notice: Subject to any disclaimer, the term of this patent is extended or adjusted under 35 U.S.C. 154(b) by 267 days.

(21) Appl. No.: 11/014,911

(22) Filed: Dec. 20, 2004

(65) Prior Publication Data

US 2005/0185247 A1    Aug. 25, 2005

(30) Foreign Application Priority Data

Dec. 25, 2003  (JP) .............................. 2003-430418

(51) Int. Cl.
*C25B 11/04* (2006.01)
(52) U.S. Cl. .................. 204/291; 429/328; 429/332; 429/343; 429/42; 359/256; 204/296
(58) Field of Classification Search .................... None
See application file for complete search history.

(56) References Cited

OTHER PUBLICATIONS

Manini et al, Acid Promoted Competing Pathways in the Oxidative Polymerization of 5, 6-Dihydroxyindoles and related Compounds: Straight forward Cyclotrimerization Routes to Diindolocarbazole Derivatives, (1998), American Chemical Society, 129:290079. See library search answer 4 of 4.*

* cited by examiner

*Primary Examiner*—Bruce F. Bell
(74) *Attorney, Agent, or Firm*—Bacon & Thomas, PLLC

(57) ABSTRACT

The present invention provides a novel indole carboxylic ester trimer which is characterized by being represented by the following general formula (1):

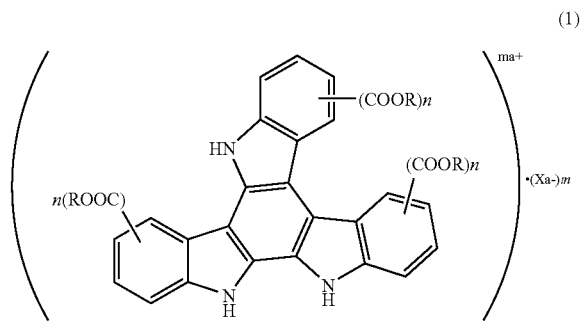

wherein R represents a straight or branched chain alkyl group having 1-6 carbon atoms; n is an integer of 1-4; $X^{a-}$ represents at least one anion selected from a group of anions having a valency of 1-3 consisting of chloride ion, bromide ion, iodide ion, fluoride ion, nitrate ion, sulfate ion, hydrogen sulfate ion, phosphate ion, borofluoride ion, perchlorate ion, thiocyanate ion, acetic acid ion, propionic acid ion, methanesulfonic acid ion, p-toluenesulfonic acid ion, trifluoroacetic acid ion and trifluoromethanesulfonic acid ion; a represents the ionic valence number of X and is an integer of 1-3; and m is 0-0.5.

5 Claims, 6 Drawing Sheets

INDOLECARBOXYLIC ESTER TRIMER AND ELECTROCHEMICAL CELL USING THE SAME

BACKGROUND OF THE INVENTION

1. Field of the Invention

This invention relates to a novel indolecarboxylic ester trimer. Compositions containing said trimer as a main ingredient are usable as an electrochemical cell, a chemical sensor, a display element, an organic EL material, anonlinear material, etc.

2. Description of the Prior Art

As trimeric derivatives of indole, 6-nitroindole trimers and 5-cyanoindole trimers have hitherto been known. These trimeric derivatives have been used as electrochemical cells using proton as electric charge carrier thereof (cf. Japanese Patent Kokai 2002-93419). On the other hand, WO 02/32903 refers to indolecarboxylic acid trimer derivatives such as indole-4-carboxylic acid trimer, indole-5-carboxylic acid trimer, indole-6-carboxylic acid trimer, indole-7-carboxylic acid trimer, and the like. However, the abovementioned WO 02/32903 gives no concrete description of indolecarboxylic ester trimers with reference to working example.

As have been mentioned above, 6-nitroindole trimer, 5-cyanoindole trimer and indole-5-carboxylic acid trimer are known as prior arts. However, it has been desired to develop a new indole trimer derivative different from the above-mentioned known ones which can give an electrode active material sufficient in electromotive force and capacity, and excellent in the cycle characteristics.

SUMMARY OF THE INVENTION

In view of above, the present inventors have conducted elaborated studies on indole trimer derivatives. As a result, it has been found, unexpectedly, a novel indolecarboxylic ester trimer has sufficiently high electromotive force and capacity as an electrochemical cell using proton as an electric charge carrier for said trimer compound and is excellent in the cycle characteristics, so that said trimer can solve the above-mentioned problem. Based on this finding, this invention has been accomplished.

Herein is provided a novel indolecarboxylic ester trimer, and an electrochemical cell containing a trimeric compound of an indole derivative and using proton as electric charge carrier, wherein said trimeric compound is the above-mentioned novel indolecarboxylic ester trimer. As referred to in this invention, "electrochemical cell" involves electric double layer condensers and secondary cells.

More specifically, the first embodiment of this invention consists in an indolecarboxylic ester trimer represented by the following general formula (1):

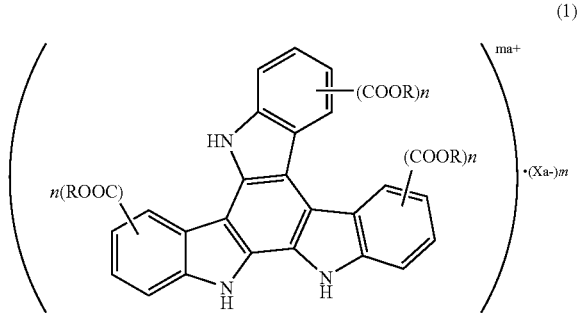

wherein R represents a straight or branched chain alkyl group having 1-6 carbon atoms; n is an integer of 1-4; $X^{a-}$ represents at least one anion selected from a group of anions having a valency of 1-3 consisting of chloride ion, bromide ion, iodide ion, fluoride ion, nitrate ion, sulfate ion, hydrogen sulfate ion, phosphate ion, borofluoride ion, perchlorate ion, thiocyanate ion, acetate ion, propionate ion, methanesulfonate ion, p-toluenesulfonate ion, trifluoroacetate ion and trifluoromethanesulfonate ion; a represents the ionic valence number of X and is an integer of 1-3; and m is 0-0.5.

The second embodiment of this invention consists in an indolecarboxylic ester trimer according to the first embodiment, wherein $X^{a-}$ is at least one anion selected from a group consisting of chloride ion, sulfate ion, borofluoride ion and perchlorate ion.

The third embodiment of this invention consists in an indolecarboxylic ester trimer according to the first or second embodiment, wherein R is methyl group.

The fourth embodiment of this invention consists in an indolecarboxylic ester trimer according to the first to third embodiments, wherein R is methyl group and the position of substitution of the carboxylic ester is the sixth position of indole.

The fifth embodiment of this invention consists in an electrochemical cell containing a trimeric compound having a linkage between the second and third positions of an indole derivative as an electrode active material and using proton as electric charge carrier of said trimeric compound, wherein said trimeric compound is an indolecarboxylic ester trimer according to the first to fourth embodiments.

DETAILED DESCRIPTION OF THE INVENTION

Figure 1:
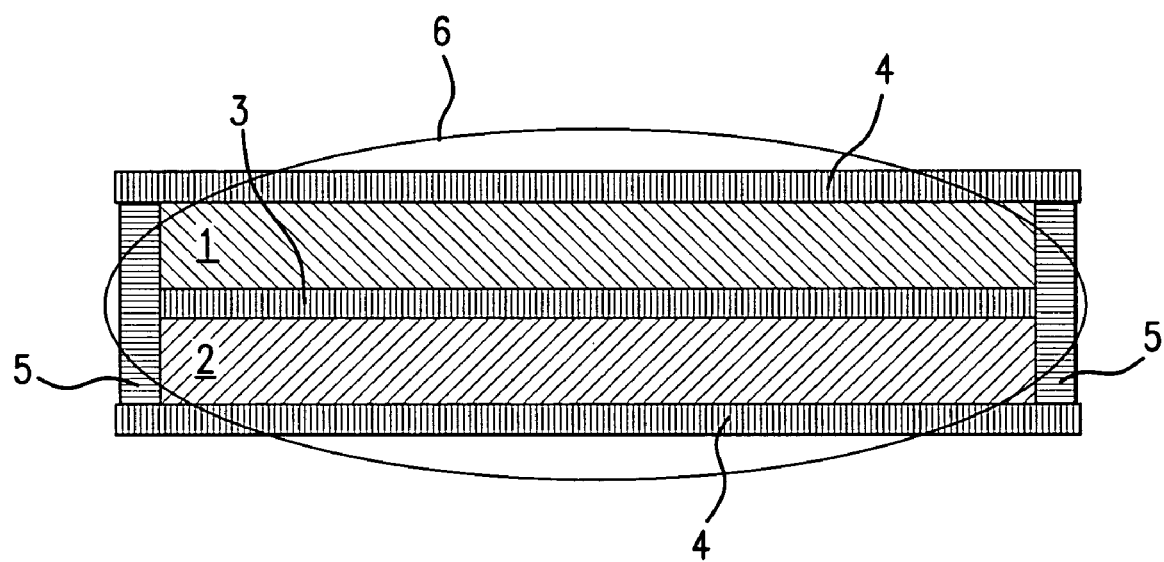
FIG. 1 is a cross-sectional view illustrating the construction of the electrochemical cell of this invention.

Hereunder, this invention will be explained in detail.

First, the indolecarboxylic ester trimer represented by general formula (1), according to this invention, will be explained.

In general formula (1), R represents a C1 to C6 alkyl group which is a straight chain or branched chain alkyl group having 1 to 6 carbon atoms such as methyl group, ethyl group, n-propyl group, isopropyl group, n-butyl group, sec-butyl group, t-butyl group, n-pentyl group, n-hexyl group and the like. R is preferably a methyl group or an ethyl group and further preferably a methyl group.

In general formula (1), n represents the number of carboxylic ester groups, which is any one integer selected from 1, 2, 3 and 4, and n is preferably 1 or 2. In the general formula (1), the position of substitution of carboxylic ester group —COOR is at least any one of the fourth, fifth, sixth and seventh positions of the indole skeleton, and preferably the fifth or sixth position, and further preferably the sixth position.

In general formula (1), $X^{a-}$ is at least one anion selected from a group of anions having a valency of 1 to 3, said group of anions consisting of chloride ion, bromide ion, iodide ion, fluoride ion, nitrate ion, sulfate ion, hydrogen sulfate ion, phosphate ion, borofluoride ion, perchlorate ion, thiocyanate ion, acetate ion, propionate ion, methanesulfonate ion, p-toluenesulfonate ion, trifluoroacetate ion and trifluoromethanesulfonate ion, and $X^{a-}$ is preferably at least one member selected from the group consisting of chloride ion, sulfate ion, borofluoride ion and perchlorate ion. In said $X^{a-}$, a represents valency number of the anion $X^{a-}$, which is an integer of 1 to 3.

Further, m represents the degree of doping of the indolecarboxylic ester trimer represented by general formula (1), which is a number of 0 to 0.5.

Further, in general formula (1), ma+ represents the valency number of the anion radical of the indolecarboxylic ester trimer represented by general formula (1), corresponding to the above-mentioned cation $X^{a-}$; and a is an integer of 1 to 3, similarly to the ion valency number of anion $X^{a-}$.

Accordingly, as concrete examples of the indole-carboxylic ester trimer represented by the general formula (1), the following can be referred to (the expression "anion" is omitted herein):

methyl indole-4-carboxylate trimer, methyl indole-5-carboxylate trimer, methyl indole-6-carboxylate trimer, methyl indole-7-carboxylate trimer, ethyl indole-4-carboxylate trimer, ethyl indole-5-carboxylate trimer, ethyl indole-6-carboxylate trimer, ethyl indole-7-carboxylate trimer, n-propyl indole-4-carboxylate trimer, n-propyl indole-5-carboxylate trimer, n-propyl indole-6-carboxylate trimer, n-propyl indole-7-carboxylate trimer, isopropyl indole-4-carboxylate trimer, isopropyl indole-5-carboxylate trimer, isopropyl indole-6-carboxylate trimer, isopropyl indole-7-carboxylate trimer, n-butyl indole-4-carboxylate trimer, n-butyl indole-5-carboxylate trimer, n-butyl indole-6-carboxylate trimer, n-butyl indole-7-carboxylate trimer, sec-butyl indole-4-carboxylate trimer, sec-butyl indole-5-carboxylate trimer, sec-butyl indole-6-carboxylate trimer, sec-butyl indole-7-carboxylate trimer, t-butyl indole-4-carboxylate trimer, t-butyl indole-5-carboxylate trimer, t-butyl indole-6-carboxylate trimer, t-butyl indole-7-carboxylate trimer, n-pentyl indole-4-carboxylate trimer, n-pentyl indole-5-carboxylate trimer, n-pentyl indole-6-carboxylate trimer, n-pentyl indole-7-carboxylate trimer, n-hexyl indole-4-carboxylate trimer, n-hexyl indole-5-carboxylate trimer, n-hexyl indole-6-carboxylate trimer, n-hexyl indole-7-carboxylate trimer, dimethyl indole-4,5-dicarboxylate trimer, dimethyl, indole-5,6-dicarboxylate trimer, dimethyl indole-6,7-dicarboxylate trimer, dimethyl indole-4,6-dicarboxylate trimer, dimethyl indole-4,7-dicarboxylate trimer, dimethyl indole-5,7-dicarboxylate trimer, trimethyl indole-4,5,6-tricarboxylate trimer, trimethyl indole-5,6,7-tricarboxylate trimer, trimethy indole-4,6,7-tricarboxylate trimer, tetramethyl indole-4,5,6,7-tetracarboxylate trimer, and the like.

Among the above-mentioned concrete examples of indole-carboxylic ester trimers represented by general formula (1), preferable are the following ones:

methyl indole-4-carboxylate trimer, methyl indole-5-carboxylate trimer, methyl indole-6-carboxylate trimer, methyl indole-7-carboxylate trimer, ethyl indole-4-carboxylate trimer, ethyl indole-5-carboxylate trimer, ethyl indole-6-carboxylate trimer, ethyl indole-7-carboxylate trimer, dimethyl indole-4,5-dicarboxylate trimer, dimethyl indole-5,6-dicarboxylate trimer, dimethyl indole-6,7-dicarboxylate trimer, dimethyl indole-4,6-dicarboxylate trimer, dimethyl indole-4,7-dicarboxylate trimer, dimethyl indole-5,7-dicarboxylate trimer, and the like.

Among the concrete examples of the indolecarboxylic ester trimers represented by general formula (1) presented above, the following ones are further preferable:

methyl indole-5-carboxylate trimer, methyl indole-6-carboxylate trimer, ethyl indole-5-carboxylate trimer, ethyl indole-6-carboxylate trimer, dimethyl indole-5,6-dicarboxylate trimer, and the like.

The indolecarboxylic ester trimers represented by the general formula (1) can be produced according to the well known methods such as the chemical trimerization described in WO 02/32903 using, as the starting compound, the corresponding indolecarboxylic ester monomer represented by the following general formula (2):

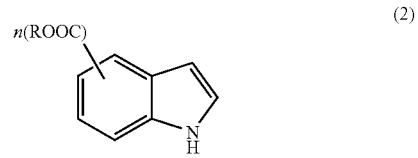

(2)

wherein R represents a straight chain or branched chain alkyl group having 1 to 6 carbon atoms, and n represents an integer of 1 to 4, or according to the electrochemical trimerization described in Journal of Electroanalytical Chemistry, 3.75 (1994) 163, etc.

In the general formula (2), R represents a hydrogen atom or a straight chain or branched chain C1 to C6 alkyl group having 1 to 6 carbon atoms such as methyl group, ethyl group, n-propyl group, isopropyl group, n-butyl group, sec-butyl group, t-butyl group, n-pentyl group, n-hexyl group and the like, and n represents an integer of 1 to 4.

As concrete examples of the indolecarboxylic ester monomer represented by the general formula (2), the following ones can be referred to:

methyl indole-4-carboxylate monomer, methyl indole-5-carboxylate monomer, methyl indole-6-carboxylate monomer, methyl indole-7-carboxylate monomer, ethyl indole-4-carboxylate monomer, ethyl indole-5-carboxylate monomer, ethyl indole-6-carboxylate monomer, ethyl indole-7-carboxylate monomer, n-propyl indole-4-carboxylate monomer, n-propyl indole-5-carboxylate monomer, n-propyl indole-6-carboxylate monomer, n-propyl indole-7-carboxylate monomer, isopropyl indole-4-carboxylate monomer, isopropyl indole-5-carboxylate monomer, isopropyl indole-6-carboxylate monomer, isopropyl indole-7-carboxylate monomer, n-butyl indole-4-carboxylate monomer, n-butyl indole-5-carboxylate monomer, n-butyl indole-6-carboxylate monomer, n-butyl indole-7-carboxylate monomer, sec-butyl indole-4-carboxylate monomer, sec-butyl indole-5-carboxylate monomer, sec-butyl indole-6-carboxylate monomer, sec-butyl indole-7-carboxylate monomer, t-butyl indole-4-carboxylate monomer, t-butyl indole-5-carboxylate monomer, t-butyl indole-6-carboxylate monomer, t-butyl indole-7-carboxylate monomer, n-pentyl indole-4-carboxylate monomer, n-pentyl indole-5-carboxylate monomer, n-pentyl indole-6-carboxylate monomer, n-pentyl indole-7-carboxylate monomer, n-hexyl indole-4-carboxylate monomer, n-hexyl indole-5-carboxylate monomer, n-hexyl indole-6-carboxylate monomer, n-hexyl indole-7-carboxylate monomer, dimethyl indole-4,5-dicarboxylate monomer, dimethyl indole-5,6-dicarboxylate monomer, dimethyl indole-6,7-dicarboxylate monomer, dimethyl indole-4,6-dicarboxylate monomer, dimethyl indole-4,7-dicarboxylate monomer, dimethyl indole-5,7-dicarboxylate monomer, trimethyl indole-4,5,6-tricarboxylate monomer, trimethyl indole-5,6,7-tricarboxylate monomer, trimethyl indole-4,6,7-tricarboxylate monomer, tetramethyl indole-4,5,6,7-tetracarboxylate monomer, and the like.

Among the concrete examples of the indolecarboxylic ester monomer represented by general formula (2), preferable are the following ones:

methyl indole-4-carboxylate monomer, methyl indole-5-carboxylate monomer, methyl indole-6-carboxylate monomer, methyl indole-7-carboxylate monomer, ethyl indole-4-carboxylate monomer, ethyl indole-5-carboxylate monomer, ethyl indole-6-carboxylate monomer, ethyl indole-7-carboxylate monomer, dimethyl indole-4,5-dicarboxylate monomer, dimethyl indole-5,6-dicarboxylate monomer, dimethyl indole-6,7-dicarboxylate monomer, dimethyl indole-4,6-dicarboxylate monomer, dimethyl indole-4,7-dicarboxylate monomer, dimethyl indole-5,7-dicarboxylate monomer, and the like.

Among the concrete examples of the indolecarboxylic ester monomer represented by the above-mentioned general formula (2), further preferable are the following ones:

methyl indole-5-carboxylate monomer, methyl indole-6-carboxylate monomer, ethyl indole-5-carboxylate monomer, ethyl indole-6-carboxylate monomer, dimethyl indole-5,6-dicarboxylate monomer, and the like.

The indolecarboxylic ester monomers represented by the general formula (2) can be produced according to the well known method expressed by, for example, the following reaction scheme:

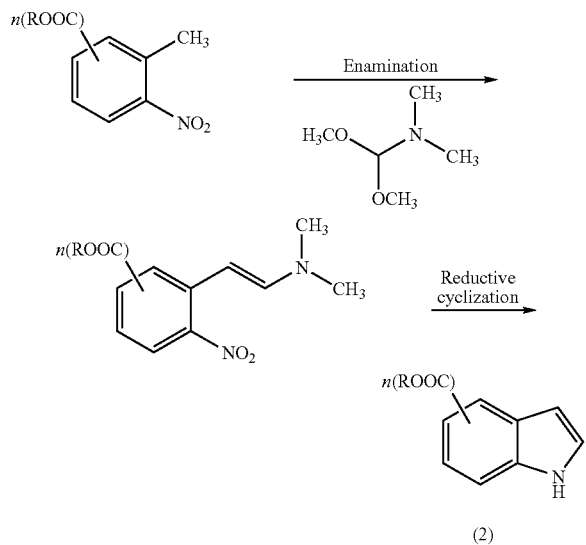

(2)

As the benzoic ester derivatives which can be used as a starting material in the enamination reaction represented by the above-mentioned reaction scheme, for example, methyl 2-methyl-3-nitrobenzoate, methyl 3-methyl-4-nitrobenzoate, methyl 4-methyl-3-nitrobenzoate, methyl 3-methyl-2-nitrobenzoate, dimethyl 5-methyl-4-nitro-1,2-benzenedicarboxylate, and the like can be referred to.

As the enaminating reagent, the generally used dimethylformamide dimethyl acetal (DMF dimethyl acetal) can be used. In this enamination reaction, the molar ratio of the starting benzoic ester derivative to the enaminating reagent may be any value. Usually, however, the enaminating reagent is used in an amount of 0.2 to 10 moles and preferably 0.8 to 3 moles, per mol of the benzoic ester derivative used as the starting material, for example.

Although this enamination reaction can sufficiently be carried out even in the absence of solvent, it is also possible to carry out this reaction in the presence of a solvent. The solvent used in this reaction may be any solvent, so far as it does not disturb the reaction. The solvents which can be used include, for example, aromatic hydrocarbons such as toluene, xylene, chlorobenzene and the like; halogenated aliphatic hydrocarbons such as dichloromethane, chloroform and the like; acetic esters such as methyl acetate, ethyl acetate, butyl acetate and the like; aprotic polar solvents such as dimethylformamide (DMF), dimethylacetamide (DMAC), N-methylpyrrolidone, tetramethylurea, hexamethyl phosphoric triamide (HMPA) and the like; ethereal solvents such as diethyl ether, tetrahydrofuran, dioxane and the like; aliphatic hydrocarbons such as pentane, n-hexane and the like; etc.; among which aprotic polar solvents such as dimethylformamide and the like are preferable.

The solvent may be put to use either in the form of a single solvent or as a mixed solvent having an arbitrary mixing ratio. As the amount of the solvent, an amount allowing a sufficient agitation of the reaction system is enough for the purpose. Usually, however, the solvent is used in an amount of 0.01 to 100 liters and preferably 0.1 to 10 liters, per mol of the benzoic ester derivative used as a starting material.

As the reaction temperature of the enamination reaction, a temperature range from 0° C. to the reflux temperature of the used solvent can be referred to, for example. However, a temperature range of from 30° C. to 200° C. is preferable. Although the reaction time is not particularly limited, a reaction time ranging from 0.1 hour to 20 hours is preferable, from the viewpoint of suppressing the formation of by-product, etc.

As the reductive cyclization reaction which is carried out next to the enamination reaction, as shown in the above-mentioned reaction scheme, known reactions which are generally adopted for the purpose of converting a nitro group to an amino group can be used. Such reactions include, for example, a catalytic reduction using gaseous hydrogen and a catalyst, and a reduction using a powdery metal such as iron, zinc, tin, etc.; beside which a method using a sulfide and a method of reduction using a formate, hydrazine, etc. in the presence of a metallic catalyst are also included.

The catalysts which can be used in the catalytic reduction method include platinum, Raney nickel, platinum black, palladium-carbon, ruthenium complex and the like. Regarding the molar ratio of the starting enamine to the catalyst, the reaction can progress at any value of the ratio [enamine/catalyst]. Usually, however, the amount of the catalyst is from 0.0001 to 0.5 mol and preferably from 0.001 to 0.2 mol, per mol of the starting enamine, for example.

This catalytic reduction reaction can be carried out in an atmosphere of hydrogen gas, under any of an ordinary pressure and an elevated pressure. An inert gas other than hydrogen may also be used simultaneously, so far as said inert gas does not disturb the reaction.

Although this catalytic reduction reaction can be carried out sufficiently in the absence of solvent, it is also possible to carry out the reaction in the presence of a solvent. Any solvents may be used in this reaction, so far as the solvents do not disturb the reaction. Examples of the solvents include aromatic hydrocarbons such as toluene, xylene, chlorobenzene and the like; halogenated aliphatic hydrocarbons such as dichloromethane, chloroform and the like; acetic esters such as methyl acetate, ethyl acetate, butyl acetate and the like; aprotic polar solvents such as dimethylformamide (DMF), dimethylacetamide (DMAC), N-methylpyrrolidone, tetramethylurea, hexamethyl phosphoric triamide (HMPA) and the like; ethereal solvents such as diethyl ether, tetrahydrofuran, dioxane and the like; aliphatic hydrocarbons such as pentane, n-hexane and the like; aliphatic alcohols such as methanol, ethanol, n-propanol, isopropanol, n-butanol, sec-butanol, tert-butanol and the like; water; and the like. Among these solvents, preferable are aliphatic alcohols such as methanol, ethanol, n-propanol, isopropanol, n-butanol, sec-butanol, tert-butanol and the like, and water.

The solvent may be used either in the form of a single solvent or as a solvent mixture having any mixing ratio. As the amount of the solvent, an amount allowing the agitation of reaction system sufficiently is enough for the purpose. Usually however, the amount of the solvent is from 0.01 to 100 liters and preferably 0.1 to 10 liters, per 1 mol of the starting enamine.

As reaction temperature of this catalytic reduction reaction, a temperature range of from 0° C. to the reflux temperature of the used solvent can be mentioned. Preferably, however, a temperature range of from 10° C. to 100° C. is adopted. Although the reaction time of this catalytic reduction reaction is not particularly limited, a reaction time of from 0.1 hour to 50 hours is preferable from the viewpoint of suppressing the formation of by-products. Additionally saying, this catalytic reduction reaction may be carried out under any of acidic condition, neutral condition and alkaline condition.

In the case of reduction using a powdered metal, the metals usable include iron, zinc, tin, and the like. Although the reaction can progress at any molar ratio of the starting enamine to the powdered metal, the amount of the catalyst is usually from 0.1 to 50.0 mol and preferably 0.5 to 10 mol, per mol of the starting enamine, for example.

Although this reduction reaction using said metallic powder can sufficiently be carried out even in the absence of solvent, it is also allowable to carry out the reaction in the presence of a solvent. Any solvents may be used so far as they do not disturb the reaction. Examples of the solvents usable include aromatic hydrocarbons such as toluene, xylene, chlorobenzene and the like; halogenated aliphatic hydrocarbons such as dichloromethane, chloroform and the like; acetic esters such as methyl acetate, ethyl acetate, butyl acetate and the like; aprotic polar solvents such as dimethylformamide (DMF), dimethylacetamide (DMAC), N-methylpyrrolidone, tetramethylurea, hexamethyl phosphoric triamide (HMPA) and the like; ethereal solvents such as diethyl ether, tetrahydrofuran, dioxane and the like; aliphatic hydrocarbons such as pentane, n-hexane and the like; aliphatic alcohols such as methanol, ethanol, n-propanol, isopropanol, n-butanol, sec-butanol, tert-butanol and the like; water; etc.

Among the above-mentioned solvents, preferable are aliphatic alcohols such as methanol, ethanol, n-propanol, isopropanol, n-butanol, sec-butanol, tert-butanol and the like; and water. The solvents can be used either in the form of a single solvent or as a solvent mixture having any mixing ratio. Although the amount of the solvent may be any amount so far as the reaction system can sufficiently be agitated at such an amount of solvent, the solvent is used usually in an amount of from 0.01 to 100 liters and preferably from 0.1 to 10 liters per mole of the starting enamine.

As the reaction temperature of the reduction using metallic powder, a temperature range from 0° C. to the reflux temperature of the used solvent can be referred to, for example. Preferably, the reaction temperature range is from 10° C. to 150° C. Although reaction time of this reaction is not particularly limited, the reaction time is preferably from 0.1 hour to 50 hours, from the viewpoint of suppressing the formation of by-products.

As the method for chemically trimerizing the indolecarboxylic ester monomer represented by general formula (2), for example, a method of making react the indolecarboxylic ester monomer represented by the general formula (2) in a solution comprising at least one kind of oxidant and at least one kind of solvent can be referred to.

The oxidants which can be used in this chemical trimerization reaction include, for example, ferric chloride hexahydrate, anhydrous ferric chloride, ferric nitrate nonahydrate, ferric nitrate, ferric sulfate n-hydrate, ferric ammonium sulfate 12-hydrate, ferric perchlorate n-hydrate, secondary ferric tetrafluoroborate, cupric chloride, cupric sulfate, cupric tetrafluoroborate, nitrosonium tetrafluoroborate, ammonium persulfate, sodium persulfate, potassium persulfate, potassium periodate, hydrogen peroxide, ozone, potassium ferrihexacyanate, tetraammonium cerium(IV) sulfate dihydrate, bromine, iodine and the like. Among these oxidants, preferable are ferric chloride hexahydrate, anhydrous ferric chloride, ferric nitrate nonahydrate, ferric nitrate, ferric sulfate n-hydrate, ferric ammonium sulfate 12-hydrate, ferric perchlorate n-hydrate, and ferric tetrafluoroborate. These oxidants may be put to use either in the form of a single agent or in combination of two or more species at any arbitrary mixing ratio.

Although the reaction can progress at any molar ratio of the indolecarboxylic ester monomer represented by general formula (2) to the oxidant, the oxidant is used usually in an amount of 0.1 to 100 mol and preferably in an amount of 1 to 50 mol, per mol of the starting indolecarboxylic ester monomer represented by general formula (2).

In this chemical trimerization reaction, any solvents may be used so far as the solvents do not disturb the reaction. Examples of the solvents which can be used include aromatic hydrocarbons such as toluene, xylene, chlorobenzene and the like; halogenated aliphatic hydrocarbons such as dichloromethane, chloroform and the like; acetic esters such as methyl acetate, ethyl acetate, butyl acetate and the like; aprotic polar solvents such as dimethylformamide (DMF), dimethylacetamide (DMAC), N-methylpyrrolidone, tetramethylurea, hexamethyl phosphoric triamide (HMPA) and the like; ethereal solvents such as diethyl ether, tetrahydrofuran, dioxane and the like; aliphatic hydrocarbons such as pentane, n-hexane and the like; aliphatic alcohols such as methanol, ethanol, n-propanol, isopropanol, n-butanol, sec-butanol, tert-butanol and the like; acetone, acetonitrile, propionitrile and the like. Among these solvents, preferable are acetone, acetonitrile, dioxane, dimethylformamide and the like.

The solvents can be used either in the form of a single solvent or as a solvent mixture having any mixing ratio. Although the amount of the solvent may be any amount so far as the reaction system can be sufficiently agitated at such an amount of solvent, the solvent is used usually in an amount of 0.01 to 100 liters and preferably in an amount of 0.1 to 10 liters, per mol of the starting indolecarboxylic ester monomer.

Preferably, this chemical trimerization reaction is carried out in the presence of the above-mentioned organic solvent and water. The amount of water used is usually 0 to 1,000 mol and preferably 0.1 to 100 mol, per mol of the starting indolecarboxylic ester monomer.

In this chemical trimerization reaction, the reaction temperature may be in a range of from 0° C. to the reflux temperature of the used solvent, for example. Preferably, the reaction temperature is in the range of from 10° C. to 100° C. In this chemical trimerization reaction, the reaction time is not particularly limited. Preferably, however, the reaction time is in the range of from 0.1 hour to 100 hours, from the viewpoint of suppressing the formation of by-products.

The method for carrying out this chemical trimerization reaction is not particularly limited. However, it is preferable to add a solution consisting of an oxidant and water or a solution consisting of an oxidant, an organic solvent and water into a mixed solution consisting of a starting indolecarboxylic ester monomer and an organic solvent.

Structure of the indolecarboxylic ester trimer of this invention obtained in the above-mentioned manner was determined by NMR measurement (apparatus for the measurement: MERCURY VX-300, manufactured by Varian Japan), IR measurement (KBr method, apparatus for the measurement: FT/IR-420, manufactured by Nippon Bunko Kogyo), and FAB-MAS measurement (matrix: m-nitrobenzyl alcohol, apparatus for the measurement: JMS-70, manufactured by JEOL).

An electrochemical cell was prepared by using the indolecarboxylic ester trimer obtained above as a positive electrode active material, and performance of the electrochemical cell was evaluated. FIG. 1 illustrates the fundamental element of the electrochemical cell used in this invention. Thus, as shown in FIG. 1, the electrochemical cell of this invention is constructed by providing positive pole layer 1 constituted of a positive electrode active material, an electroconductive assistant and a binder and negative pole layer 2 constituted of a negative electrode active material, an electroconductive assistant and a binder so that the positive pole layer 1 and the negative pole layer 2 stand face-to-face through intermediation of separator 3 constituted of a polyolefin type porous membrane, an ion-exchange membrane, or the like. As the electrolytic solution, an aqueous or non-aqueous solution containing a proton source is filled. Outside the electrolytic solution, a current collector 4 and a gasket 5 are provided and the outside is sealed. Hereunder, the method for preparing this electrochemical cell will be described concretely.

The positive pole layer 1 is a solid electrode prepared by adding, to indolecarboxylic ester trimer of this invention used as the positive electrode active material, 20% by weight of a gaseous phase-grown carbon as an electroconductive assistant and 8% by weight of polyvinylidene fluoride (average molecular weight: 1,100) as, an electrode-forming agent, followed by agitating and mixing the mixture by means of a blender, and forming the blended mixture to a prescribed size by means of a hot press.

On the other hand, the negative pole layer 2 is a solid electrode prepared by adding 25% by weight of a gas phase-grown carbon as an electroconductive assistant to polyphenylquinoxaline which is a negative electrode active material represented by the following formula:

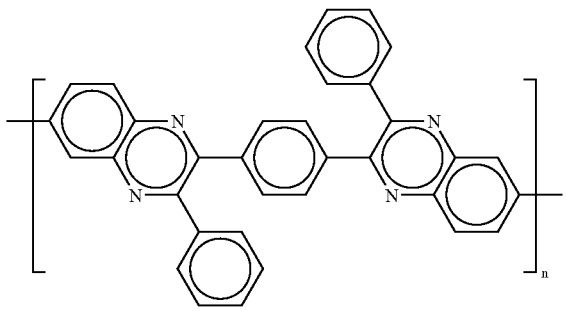

and then stirring and mixing the resulting mixture by means of a blender and forming the blended mixture by means of a hot press, so that the blended mixture was formed into prescribed size.

A fundamental element 7 was prepared by face-to-face providing positive electrode layer 1 and negative electrode layer 2 both of which have previously been impregnated with an electrolytic solution, through intermediation of separator 3, followed by sealing the outside by means of the current collector 4 and gasket 5. Using 20% by weight aqueous solution of sulfuric, acid as the electrolytic solution, cycle characteristics were evaluated by using this fundamental element 6. Temperature of the evaluation was 45° C.

EXAMPLES

Hereunder, this invention is explained concretely by referring to preparation examples and working examples. This invention is by no means limited by these examples.

Preparation Example 1

Synthesis of Methyl 4-Dimethylaminovinyl-3-Nitrobenzoate

Into a reaction flask were introduced 89.7 g of methyl 4-methyl-3-nitrobenzoate, 82.1 g of dimethylformamide dimethyl acetal and 200 ml of dimethylformamide (DMF), and the content of the flask was stirred at 120° C. for 6 hours. DMF was distilled off to obtain a red-violet colored solid product. Then, 300 ml of methanol was poured into the flask to wash the crystalline matter, and filtered. Thus, 104.8 g (yield 91%) of methyl 4-dimethylaminovinyl-3-nitrobenzoate was obtained.

Preparation Example 2

Synthesis of Methyl Indole-6-Carboxylate Monomer—Catalytic Reduction Method

Into a reaction flask were introduced 87.1 g of methyl 4-methyl-3-nitrobenzoate, 400 ml of methanol and 8 g of 5% palladium-carbon (Pd/C). The content of the flask was stirred at room temperature for 12 hours in an atmosphere of hydrogen at ordinary pressure. The Pd/C was removed by filtration, and methanol was distilled out from the filtrate to obtain a slightly yellow colored solid product. The product was dissolved in ethyl acetate, washed with 5% aqueous solution of NaOH, washed with 5% aqueous solution of hydrochloric acid and water, and the ethyl acetate was distilled off. Thus, 50.4 g (yield 68.7%) of methyl indole-6-carboxylate monomer was obtained.

Preparation Example 3

Synthesis of Methyl Indole-6-Carboxylate Monomer—Iron Powder Reduction Method

Into a reaction flask were introduced 176.4 g of iron powder, 43.5 g of acetic acid, 71.2 g of water and 273.3 g of toluene. The content of the flask was heated to 80° C. Then, a solution of 131.8 g of methyl 4-methyl-3-nitrobenzoate in 110.4 g of DMF was dropwise added into the above-mentioned mixed solution over a period of about one hour, after which the resulting mixture was stirred for an additional 4 hours at 80° C. After cooling the reaction mixture, the solid material was removed by filtration. The filtrate was washed with 5% aqueous solution of NaOH, and washed with 5% aqueous solution of hydrochloric acid and water, and then the toluene was distilled off to obtain a brown-colored solid product. Then, 164.3 g of cyclohexane was added to dissolve the solid product at about 80° C. The resulting solution was cooled to room temperature, and the deposited crystalline material was collected by filtration and dried to obtain 73.8 g (yield 80.0%) of methyl indole-6-carboxylate monomer.

Example 1

Synthesis of Methyl Indole-6-Carboxylate Trimer

Into a reaction flask were introduced 32.6 g of methyl indole-6-carboxylate monomer and 108 g of acetonitrile. The content of the flask was heated to 65° C. To the above-mentioned mixed solution, a solution prepared by dissolving 301.5 g of anhydrous ferric chloride in 652 g of acetonitrile and 100.5 g of water was dropwise added over a period of about 4 hours, and the resulting mixture was stirred at 65° C. for an additional 2 hours. After cooling the mixture thus prepared to room temperature, the deposited crystalline material was collected by filtration to obtain a deep green-colored solid product. To the solid product was added 69.8 g of 20% aqueous solution of sulfuric acid, the resulting mixture was stirred for about 2 hours, and then the crystalline material was collected by filtration to obtain a deep green-colored solid product. After adding 46.5 g of water to this solid product and stirring the resulting mixture for about 2 hours, the crystalline product was collected by filtration to obtain a green-colored solid product. Then, 3.68 g of methanol was added to this solid product and the resulting mixture was stirred for about 2 hours, and the crystalline material was collected by filtration and dried. Thus, 25.8 g (yield 80.1%) of trimethyl 6,11-dihydro-5H-diindolo[2,3-a:2',3'-c]carbazole-3,8,13-tricarboxylate (methyl indole-6-carboxylate trimer) was obtained.

Figure 2:
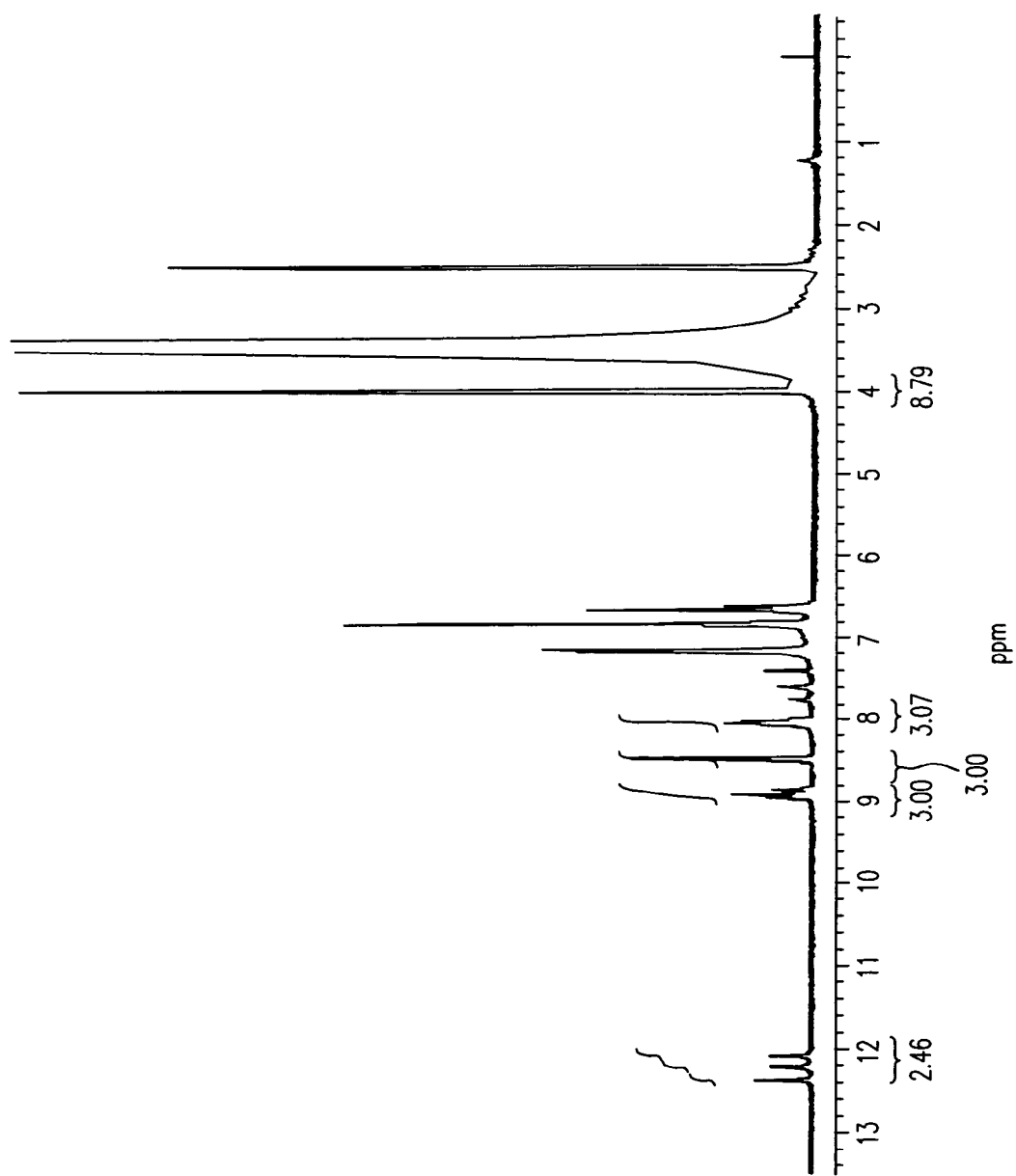
FIG. 2 is a drawing illustrating the $^1$H-NMR spectrum of the methyl indole-6-carboxylate trimer synthesized in Example 1.
Figure 3:
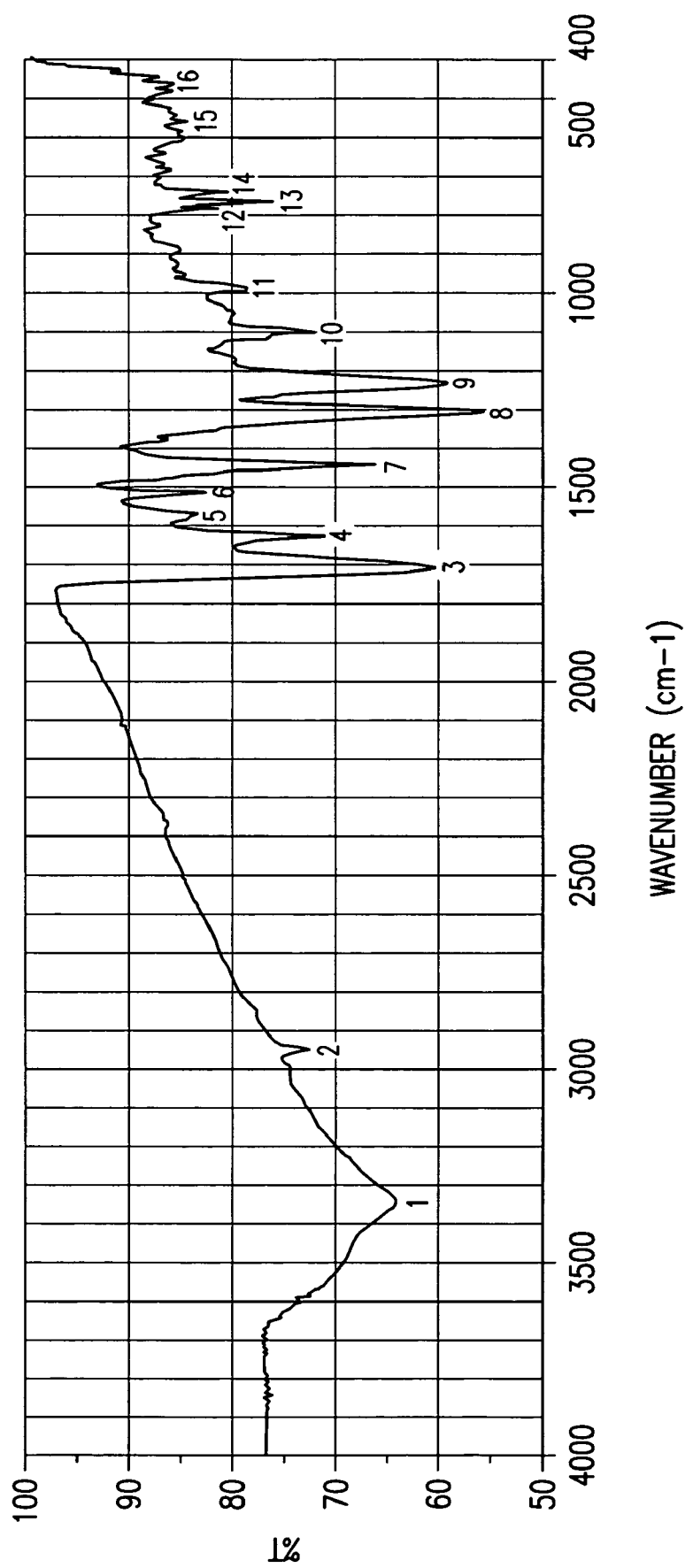
FIG. 3 is a drawing illustrating the IR spectrum of the methyl indole-6-carboxylate trimer synthesized in Example 1.

Structure of the trimethyl 6,11-dihydro-5H-diindolo[2,3-a:2',3'-c]carbazole-3,8,13-tricarboxylate (methyl indole-6-carboxylate trimer) was confirmed by $^1$H-NMR shown in FIG. 2, IR shown in FIG. 3 and FAB-MS (M−1=518). Since a part of the compounds obtained according to this example formed a cation radical in which the anion was doped, their direct NMR measurement gave merely a broad peak. Accordingly, their NMR measurement was carried out after adding phenylhydrazine to convert them into a de-doped form.

Example 2

Synthesis of Dimethyl Idole-5,6-Dicarboxylate Trimer

Figure 4:
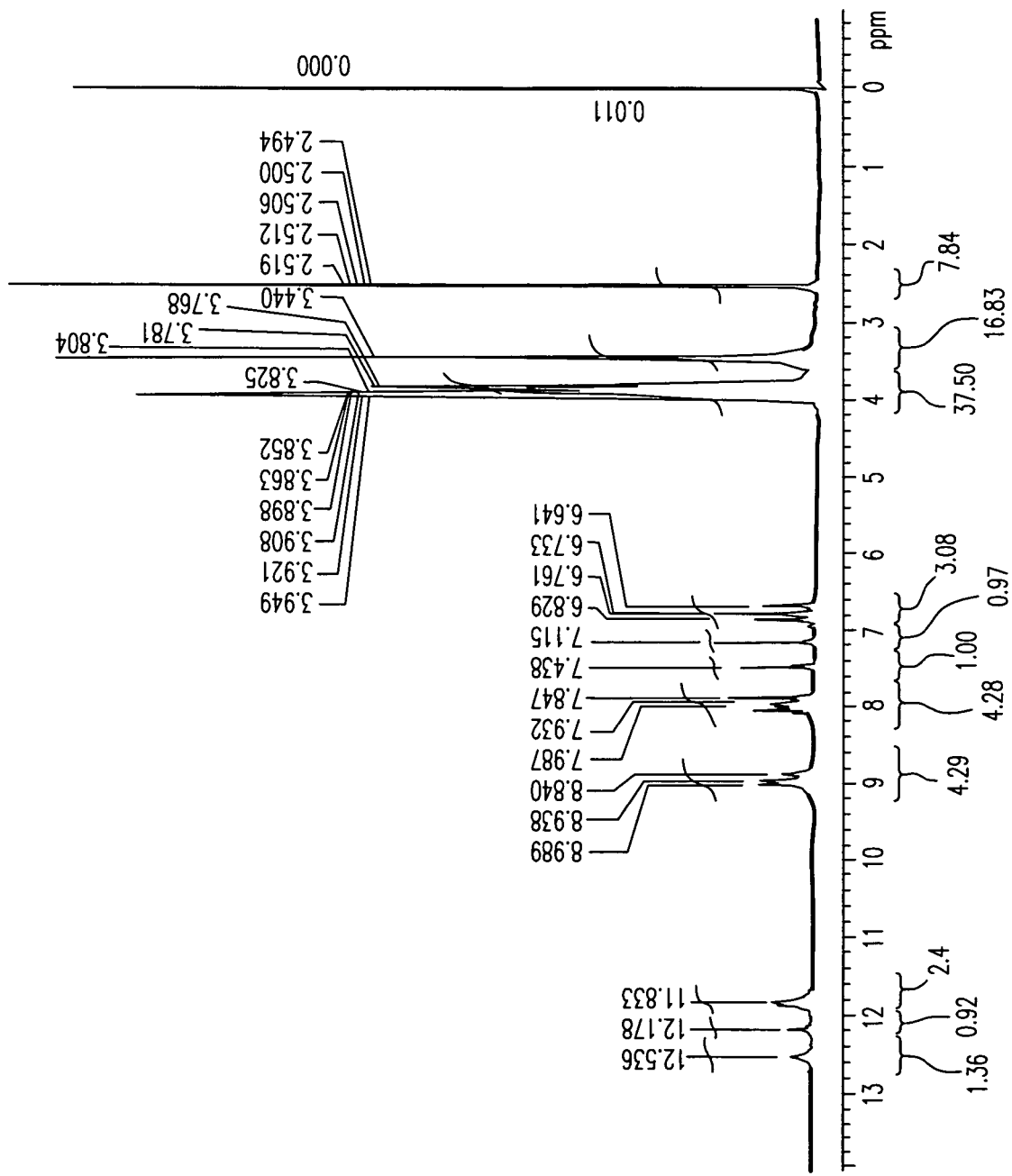
FIG. 4 is a drawing illustrating the $^1$H-NMR spectrum of the dimethyl indole-5,6-dicarboxylate trimer synthesized in Example 2.
Figure 5:
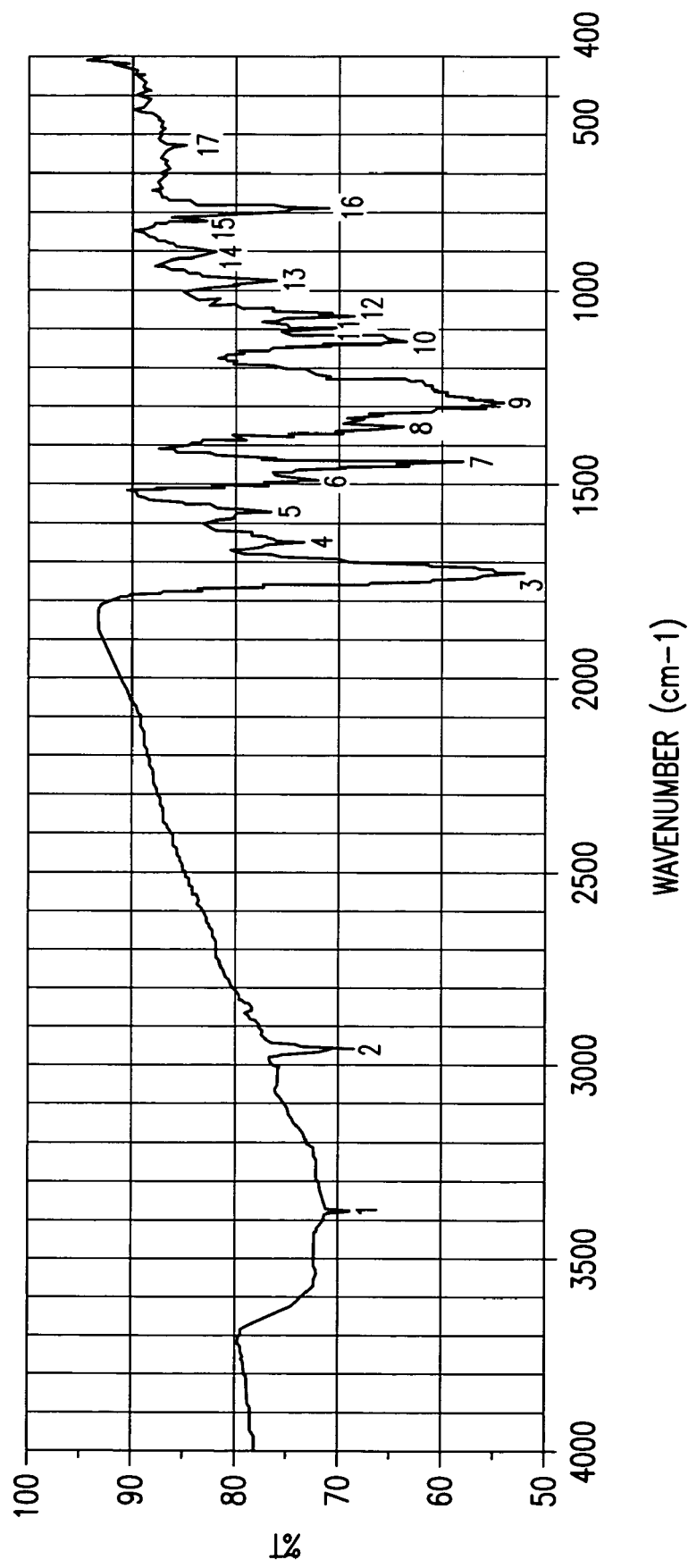
FIG. 5 is a drawing illustrating the IR spectrum of the dimethyl indole-5,6-dicarboxylate trimer synthesized in Example 2.

Into a reaction flask were charged 4.7 g of dimethyl indole-5,6-dicarboxylate monomer and 18 g of acetonitrile, and the content of the flask was heated to 50° C. Then, a solution prepared by dissolving 27.7 g of ferric perchlorate n-hydrate in 120 g of acetonitrile was dropwise added to the solution obtained above over a period of about 2 hours, and the resulting mixture was stirred at 50° C. for 24 hours. After cooling the mixture to room temperature, the deposited crystalline material was collected by filtration to obtain a deep green-colored solid product. After adding 10 g of 20% aqueous solution of sulfuric acid to the solid product and stirring the mixture for about 2 hours, the crystalline matter was collected by filtration to obtain a deep green-colored solid product. After adding 10 g of water to the solid product obtained herein and stirring the mixture for about 2 hours, the crystalline material was collected by filtration to obtain a green-colored solid product. After adding 10 g of methanol to this solid product and stirring the resulting mixture for about 2 hours, the crystalline product was collected by filtration and dried. Thus, 2.6 g (yield 55.8%) of hexamethyl 6,11-dihydro-5H-diindolo[2,3-a:2',3'-c]carbazole-2,3,8,9,13,14-hexacarboxylate (dimethyl indole-5,6-dicarboxylate trimer) was obtained. Structure of this product was confirmed by $^1$H-NMR shown in FIG. 4, IR shown in FIG. 5 and FAB-MS (M−1=692).

Example 3

Figure 6:
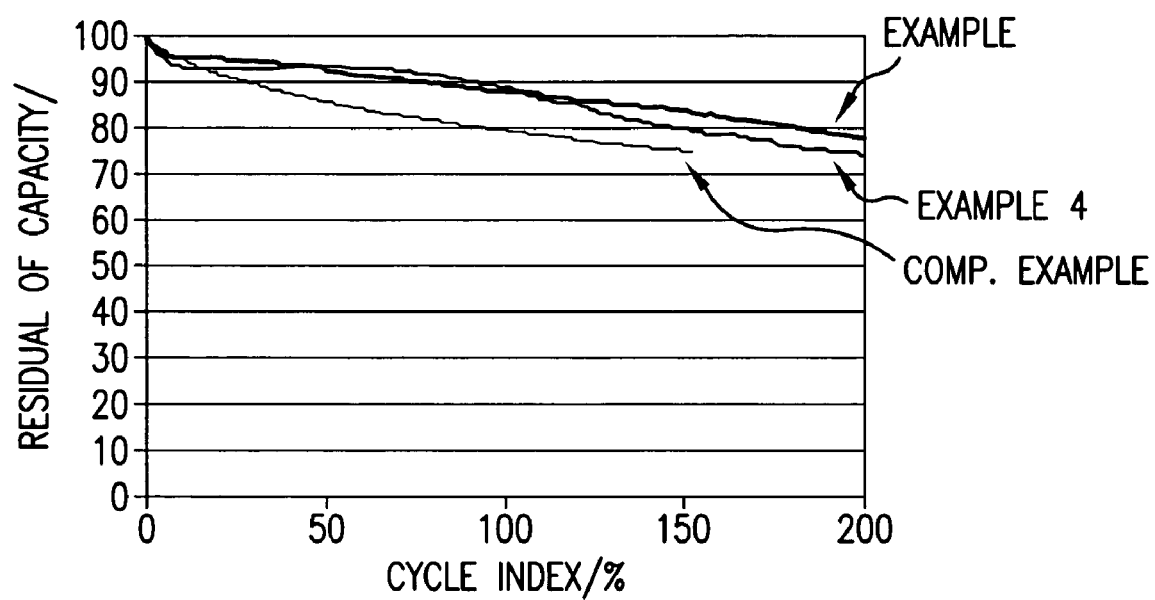
FIG. 6 is a drawing illustrating the evaluation of charging-discharging cycle characteristics on the electrochemical cells of Example 3, Example 4 and Comparative Example 1.

Preparation of Electrochemical Cell Using Methyl Indole-6-Carboxylate Trimer as a Positive Electrode Active Material and Charging-Discharging Test Thereof An electrochemical cell having the above-mentioned construction was prepared by using methyl indole-6-carboxylate trimer as a positive electrode active material. In order to evaluate the change in the capacity of the electrochemical cell thus prepared in charging-discharging cycle, evaluation of the charging-discharging cycle characteristics was carried out. The results of the evaluation are shown in FIG. 6.

Example 4

Preparation of Electrochemical Cell Containing Dimethyl Indole-5,6-Dicarboxylate Trimer as Positive Electrode Active Material and Charging-Discharging Test An electrochemical cell having the above-mentioned construction was prepared by using indole-5,6-dicarboxylate trimer as a positive electrode active material in order to evaluate the change in capacity of the electrochemical cell obtained above in a charging-discharging cycle, evaluation of the charging-discharging cycle characteristics was carried out. The results of the evaluation are shown in FIG. 6.

Comparative Example 1

Preparation of Electrochemical Cell Using Indole-5-Carboxylate Trimer as Positive Electrode Active Material and Charging-Discharging Test Thereof An electrochemical cell having the above-mentioned construction was prepared by using indole-5-carboxylic acid trimer as a positive electrode active material. In order to evaluate the change in the capacity of the electrochemical cell thus prepared in charging-discharging cycle, evaluation of the charging-discharging cycle characteristics was carried out. The results of the evaluation are shown in FIG. 6.

In calculating the cycle index (%) shown in FIG. 6, the cycle number at which the capacity of the electrochemical cell of Comparative Example 1 has reached 80% of the initial capacity was taken as 100, and the residual rate of capacity shown in the ordinate was calculated by taking the capacity of the first cycle as 100. As is apparent from this result, the electrochemical cell of Example 3 is improved in the cycle characteristics by 80% as compared with the electrochemical cell of Comparative Example 1, and the electrochemical cell of Example 4 is improved in the cycle characteristics by 50% as compared with the electrochemical cell of Comparative Example 1.

According to this invention, a novel indolecarboxylic ester trimer is provided. The novel indolecarboxylic ester trimer provided by this invention has a sufficient electromotive force and capacity as an electrochemical cell using proton as a charge carrier of said trimeric compound, and is superior in the cycle characteristics. Therefore, this invention has a high industrial utilizability.

What is claimed is:

1. An indolecarboxylic ester trimer represented by the following general formula [1]:

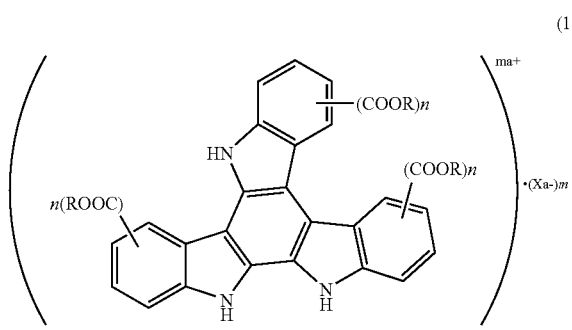

wherein R represents a straight or branched chain alkyl group having 1 to 6 carbon atoms; n represents an integer of 1 to 4; $X^{a-}$ represents at least one anion selected from the group consisting of anions having a valency of 1 to 3, said group comprising chloride ion, bromide ion, iodide ion, fluoride ion, nitrate ion, sulfate ion, hydrogen sulfate ion, phosphate ion, borofluoride ion, perchlorate ion, thiocyanate ion, acetate ion, propionate ion, methanesulfonate ion, p-toluenesulfonate ion, trifluoroacetate ion and trifluoromethanesulfonate ion; a represents an integer of 1 to 3 which represents the ionic valence number of X; and m represents a number of 0 to 0.5.

2. An indolecarboxylic ester trimer according to claim 1, wherein $X^{a-}$ is at least one anion selected from the group consisting of chloride ion, sulfate ion, borofluoride ion and perchlorate ion.

3. An iodolecarboxylic ester trimer according to claim 1, wherein R is a methyl group.

4. An indolecarboxylic ester trimer according to any one of claims 1, wherein R is a methyl group, and the position of substitution of the carboxylic ester is the 6-th position of indole.

5. An electrochemical cell containing a trimeric compound having a linkage between the second and the third positions of an indole derivative as an electrode active material and using proton as the electric charge carrier of said trimeric compound, wherein said trimer is an indolecarboxylic ester trimer according to any one of claims 1.

* * * * *